United States Patent [19]
Marchetti et al.

[11] Patent Number: 5,156,625
[45] Date of Patent: Oct. 20, 1992

[54] ACETABULAR PROSTHESIS HAVING A METAL SUPPORTING SHELL

[75] Inventors: Pier G. Marchetti, Bologna, Italy; Rudolf Koch, Berlingen; Willi Frick, Wabern, both of Switzerland

[73] Assignees: Sulzer Brothers Limited, Sinterthur; Protek AG, Berne, both of Switzerland

[21] Appl. No.: 589,064

[22] Filed: Sep. 27, 1990

[30] Foreign Application Priority Data

Sep. 28, 1989 [CH] Switzerland .......................... 3524/89

[51] Int. Cl.$^5$ ................................. A61F 2/34
[52] U.S. Cl. .................................... 623/22
[58] Field of Search ........................ 623/16, 18, 22, 23

[56] References Cited

U.S. PATENT DOCUMENTS 4,883,491 11/1989 Mallory et al. ...................... 623/22
4,904,265 2/1990 MacCollum et al. ................ 623/22

FOREIGN PATENT DOCUMENTS 0380045 8/1989 European Pat. Off. ............. 623/22
0340175 11/1989 European Pat. Off. ............. 623/22
0341199 11/1989 European Pat. Off. ............. 623/22

Primary Examiner—David Isabella
Attorney, Agent, or Firm—Kenyon & Kenyon

[57] ABSTRACT

The acetabular prosthesis includes a metal supporting shell having collar-shaped projections which have tapered cutting edges for penetrating into the osseous tissue of a pelvic bone. The distal portions of the projections are tapered so that plugs of bone can be formed upon penetration of the projections into the osseous tissue. The projections may be filled with bone chips prior to fitting in of a plastic shell within the metal supporting shell. A multi layer metal mesh is provided on the outer surface of the metal shell for promoting fusion. If the overall attachment is not adequate, the projections can be used for insertion and centering of bone screws.

9 Claims, 2 Drawing Sheets

ACETABULAR PROSTHESIS HAVING A METAL SUPPORTING SHELL

This invention relates to an acetabular prosthesis. More particularly, this invention relates to an acetabular prosthesis having a metal supporting shell for securement in a pelvis without the use of cement.

As is known, various types of acetabular prosthesis have been provided for implantation in pelvic bones. For example, European Patent Application 0 212 087 describes an acetabular prosthesis having a plastic shell which is covered by a multi-layer metal mesh and which is provided with pins which are embedded in and which project from the plastic shell. Each pin is further provided with a central bore and lateral openings in order to effect implantation of the acetabular prosthesis in a pelvic bone. European Patent Application 0 121 002 describes an acetabular prosthesis which is provided with expandable ribbed projections which can be expanded upon the threading in of bone screws. German O.S. 32 05 526A1 describes a metal shell for an acetabular prosthesis which employs hollow plugs which pass through the shell for anchorage in a pelvic bone. Similar structures are also described in French Patent 8200761. In these latter cases, the shells provide templates for positioning location holes in the hip joint region. International Patent Application WO85/02535 describes various types of artificial joint cavities employing hollow cylindrical members which can be threaded into a pelvic bone, for example, through openings in an outer shell of an acetabular prosthesis. However, these constructions require an initial placement of the shell and the use of the shell as a template prior to insertion of such hollow bodies.

Generally, the object for acetabular prosthesis is to achieve a good attachment in the osseous tissue of the pelvis, on the one hand, primarily for immediate loading and, on the other hand, for the fusion (ingrowth) of osseous tissue.

Accordingly, it is an object of the invention to provide a metal supporting shell for an acetabular prosthesis which produces a positioning control and an attachment.

It is another object of the invention to provide a metal supporting shell for an acetabular prosthesis which provides an initial positioning control and which enables the attachment to be strengthened after insertion of the supporting shell in a pelvis.

It is another object of the invention to provide a relatively simple acetabular prosthesis construction for insuring primary attachment in a pelvic bone.

Briefly, the invention provides an acetabular prosthesis which includes a metal supporting shell having at least one outwardly directed collar-shaped projection defining an opening through the shell wherein the projection has a tapered cutting edge for penetrating into osseous tissue in the pelvic bone. In addition, the projection has an annular distal portion having the cutting edge thereon which is conically disposed inwardly about an axis of the projection for penetrating into the osseous tissue.

The metal shell is made from deep-drawn sheet metal and preferably includes a pair of collar-shaped projections disposed in non-symmetric manner about a central opening in the shell.

One advantage of the metal shell is that, with the insertion of the collar-shaped projections, plugs of osseous tissue remain within the projections. These plugs can be used to promote fusion (ingrowth of osseous tissue) inside the projection so that the tissue forms an expanding plug which then acts as a mechanical retaining device. Also, after insertion, if the plugs of osseous tissue are not sufficient, the projections may be used as bore holes so as to receive retaining screws. In this respect, after the insertion of the supporting shell, a decision can be made on the basis of the position, i.e. the retaining action of the osseous tissue, whether additional retaining elements are required which can be mounted without much preparation.

Another advantage of the shell lies in the construction of the shell which is of light weight construction and can be adapted to mass production by using deformable sheet metal as the base material.

These and other objects and advantages of the invention will become more apparent from the following detailed description taken in conjunction with the accompanying drawings wherein:

FIG. 3 illustrates a plan view of the acetabular prosthesis of FIG. 1; and

Figure 1:
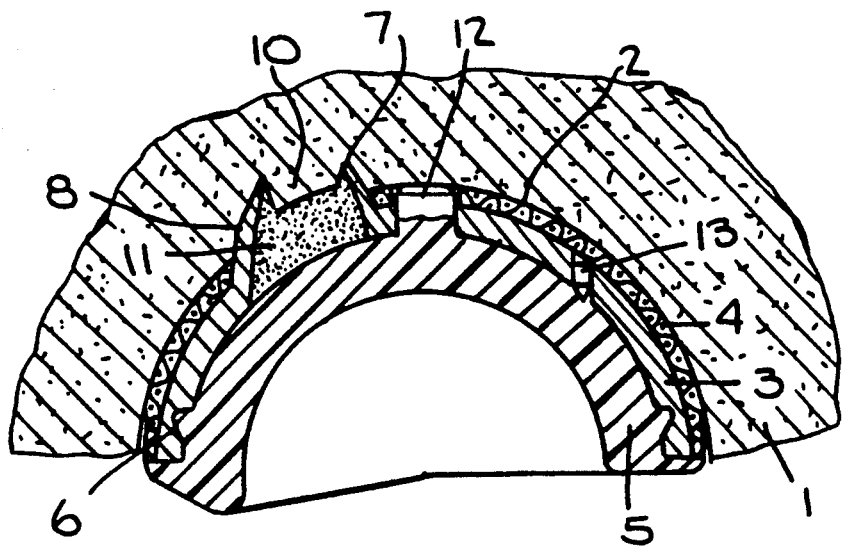
FIG. 1 illustrates a cross sectional view of an acetabular prosthesis according to the invention implanted in place.

Referring to FIG. 1, the acetabular prosthesis is constructed for securement in the osseous tissue 1 of a pelvis without the use of cement. As indicated, the acetabular prosthesis is formed of a metal supporting shell 3, a multi-layer metal mesh 4 disposed over an outer surface of the shell 3 and a plastic shell 5 secured within the metal shell 3.

Referring to FIG. 1, the metal supporting shell 3 is made of sheet metal and is of a part-spherical shape, e.g. a hemispherical shape, for mounting in the osseous tissue 1 of the pelvic bone. In addition, the shell 3 has a pair of outwardly directed integral collar-shaped projections 8 as well as a central opening on an axis thereof. As indicated in FIG. 3, the two projections 8 are disposed in non-symmetric relation relative to the axis of the shell 3, for example, both being disposed on one side of a vertical diametric plane through the axis of the shell 3, as viewed.

Each projection 8 has a tapered cutting edge 7 for penetrating into the osseous tissue 1. In addition, each cutting edge 7 is disposed on an annular distal portion of the projection 8 which is conically disposed inwardly about an axis of the projection. When inserted, each projection 8 becomes embedded in the osseous tissue 1 and with the outer surface forms an attachment to prevent the supporting shell 3 from slipping. At the same time, a plug of bone 10 remains within the projection 8. In this respect, the actual attachment is formed by the undercut outer edge of the supporting shell 3 on which the metal mesh 4 is positioned and is held by the osseous tissue 1. If the supporting shell 3 is adequately secured, the space around the plug of bone 10 in each projection 8 is filled with bone chips and granulated powder of hydoxyapatite 11 prior to insertion of the plastic shell 5. In addition, as indicated in FIG. 2, each projection 8 is provided with openings 9 for the ingrowth of tissue and to permit the plugs of bone 10 to fuse better.

Figure 2:
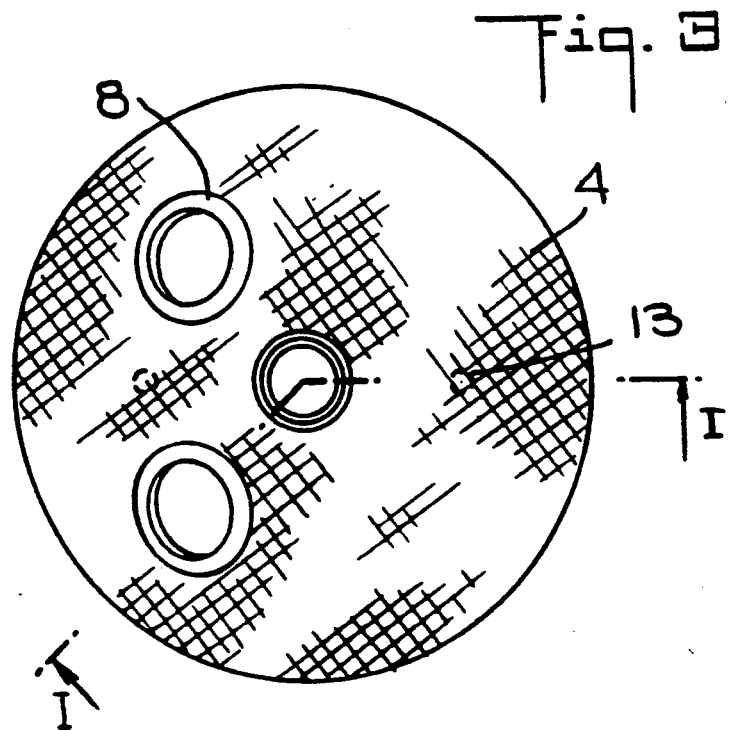
FIG. 2 illustrates a lateral elevational view of the acetabular prosthesis of FIG. 1.
Figure 2:
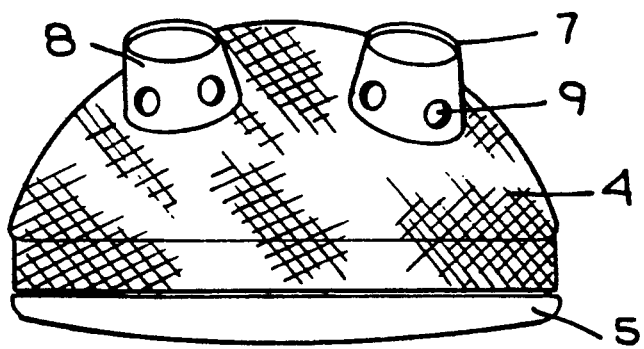

As indicated in FIGS. 2 and 3, the metal mesh 4 for promoting fusion is disposed over the entire surface of the supporting shell 3 and about the projections 8, each of which projects through the mesh 4.

The plastic shell 5 has a centrally disposed plug 12 for fitting into the opening of the metal shell 3 for guiding of the shell 5 into place. As indicated, a spring catch 6 is provided for securing the plastic shell 5 in the metal shell 3. Any suitable securing means may also be used for the securement of the plastic shell 5 in the metal shell 3.

Figure 4:
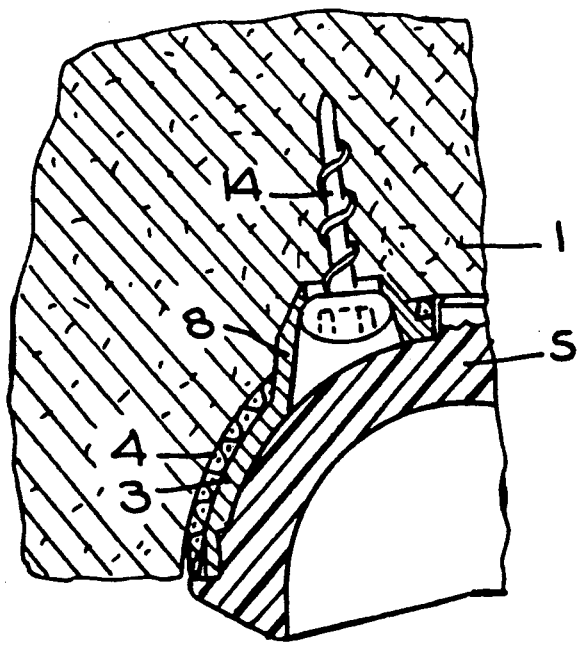
FIG. 4 illustrates a detail view of the acetabular prosthesis employing a retaining screw in accordance with the invention.

Referring to FIG. 1, in order to secure the acetabular prosthesis in place, the metal supporting shell 3 with the metal mesh 4 thereon is first forced into a spherical recess 2 in the pelvis without the use of bone cement. During this time, the cutting edges 7 of the projections 8 penetrate into the osseous tissue 1 to provide a primary fixation of the shell within the osseous tissue 1. If the supporting shell 3 is not adequately secured, the plugs of bone 10 are removed and bone screws are inserted. In this respect, as indicated in FIG. 4, each bone retaining screw 14 is provided with a head which abuts on the conically disposed distal portion of each projection 8 to secure the supporting shell 3 in place.

After attachment of the metal shell 3, the bone chips and granulated hydoxyapatite powder 11 are placed in the cavities defined by the projections 8 about the respective bone plugs 10.

After the anchorage of the metal shell 3, the plastic shell 5 is roughly centered via the plug 12 and pushed into place and held therein by means of the spring catch 6.

Referring to FIGS. 1 and 3, in order to prevent rotation between the supporting shell 3 and the plastic shell 5, a pair of pins 13 which are secured to the metal shell 3 penetrate into the plastic shell 5 after the spring catch 6 has been engaged.

The invention thus provides a metal supporting shell for an acetabular prosthesis which can be readily secured in place in a pelvic bone to provide for primary anchorage of the remaining components of the acetabular prosthesis.

Further, the invention provides a supporting shell which can be readily manufactured in mass produced quantities.

What is claimed:

1. An acetabular prosthesis comprising
a metal supporting shell having a plurality of outwardly directed collar-shaped projections for penetrating into osseous tissue in a pelvic bone, each projection having a projecting tapered cutting edge;
a multi-layer metal mesh on a surface of said shell for promoting fusion, said mesh being disposed about said projections with said projections projecting through said mesh; and
a plastic shell secured in said metal shell.

2. An acetabular prosthesis as set forth in claim 1 wherein each projection has an annular distal portion with a tapered cutting edge directed inwardly of a central axis thereof.

3. A metal supporting shell for an acetabular prosthesis having a part-spherical shape for mounting in a pelvic bone and at least one outwardly directed collar-shaped projection defining an opening through said shell, said projection having a tapered cutting edge for penetrating into osseous tissue in the pelvic bone to provide a primary fixation in the tissue while forming a plug of bone within said projection;
a metal mesh disposed over an outer surface of said shell said mesh being disposed about said projections with said projections projecting trhough said mesh.

4. A shell as set forth in claim 3 made of sheet metal.

5. A shell as set forth in claim 3 wherein said projection has an annular distal portion having said cutting edge thereon, said distal portion having a conical cross-section and being directed inwardly about an axis of said projection.

6. An acetabular prosthesis, comprising
a metal supporting shell having a part-spherical shape for mounting in a pelvic bone and at least one outwardly directed collar-shaped projection defining an opening through said shell, said projection having a tapered cutting edge for penetrating into osseous tissue in the pelvic bone to provide a primary fixation;
a metal mesh disposed over an outer surface of said shell said mesh being disposed about said projections with said projections projecting through said mesh; and
a plastic shell secured in said metal shell.

7. An acetabular prosthesis as set forth in claim 6 wherein said metal shell has a central opening on an axis thereof and a pair of said projections disposed in non-symmetric relation relative to said axis and wherein said plastic shell has a centrally disposed plug for fitting into said opening of said metal shell.

8. An acetabular prosthesis as set forth in claim 7 which further comprises at least one pin secured to said metal shell and penetrating into said plastic shell to prevent relative rotation between said shells.

9. An acetabular prosthesis as set forth in claim 6 wherein said projection has a plurality of openings for ingrowth of tissue.

* * * * *